(12) United States Patent
Amey et al.

(10) Patent No.: US 6,924,394 B2
(45) Date of Patent: Aug. 2, 2005

(54) LOW PRESSURE PROCESS FOR THE MANUFACTURE OF 2-(AMINOMETHYL)-1-CYCLOPENTYLAMINE

(75) Inventors: Ronald L. Amey, Wilmington, DE (US); Ronald H. Mattson, Jr., Wilmington, DE (US)

(73) Assignee: Invista North America S.r.l., Wilmington, DE (US)

( * ) Notice: Subject to any disclaimer, the term of this patent is extended or adjusted under 35 U.S.C. 154(b) by 246 days.

(21) Appl. No.: 10/455,706

(22) Filed: Jun. 5, 2003

(65) Prior Publication Data
US 2004/0249214 A1 Dec. 9, 2004

(51) Int. Cl.$^7$ ............................................ C07C 211/17
(52) U.S. Cl. ...................................................... 564/453
(58) Field of Search ......................................... 564/453

(56) References Cited

U.S. PATENT DOCUMENTS 2,292,949 A    8/1942  Lazier et al.
3,862,911 A  * 1/1975  Chabert ...................... 502/301
6,251,229 B1 * 6/2001  Luyken et al. ................. 203/91

FOREIGN PATENT DOCUMENTS

GB    1 397 576    12/1972

OTHER PUBLICATIONS

Klenke, Burkhard and Gilbert, Ian. Nitirle Reduction in the Presence of Boc–Protected Amino Groups by Catalytic Hydrogenation over Palladium–Activated Raney–Nickel. Sep. 6, 2000. J. Org. Chem. 2001, 66, 2480–2483.

Thompson, Quentin E., Adiponitrile—a Novel Self–condensation Sequence. May 8, 1958.

* cited by examiner

Primary Examiner—Golam M M Shameem

(57) ABSTRACT

Disclosed herein is a process for the manufacture of 2-(aminomethyl)-1-cyclopentylamine by low-pressure hydrogenation of 1-amino-2-cyano-1-cyclopentene using a combination catalyst system of nickel with palladium on carbon, or a single palladium-doped Raney-type catalyst.

7 Claims, No Drawings

LOW PRESSURE PROCESS FOR THE MANUFACTURE OF 2-(AMINOMETHYL)-1-CYCLOPENTYLAMINE

FIELD OF THE INVENTION

Described herein is the selective, low pressure hydrogenation of 1-amino-2-cyano-1-cyclopentene (CPI) to 2-(aminomethyl)-1-cyclopentylamine (AMC) by a combined catalyst system comprising nickel in combination with palladium on carbon, or a single palladium-doped Raney-type catalyst.

BACKGROUND OF THE INVENTION 2-(aminomethyl)-1-cyclopentylamine (AMC) was first reported by Lazier and Howk, described in U.S. Pat. No. 2,292,949, who prepared the diamine by hydrogenation of CPI at 2000–3000 psi $H_2$, 120° C. using either a nickel on alumina or finely divided, unsupported cobalt catalyst. The yield using Ni was 36% and 59% using Co. A hydrogen gas pressure of at least 1500 psi was used for the reaction in the presence of a Group VIII metal catalyst.

In GB 1397576 Chabert describes a process for the catalytic hydrogenation of CPI in the presence of a powdered Raney-type catalyst containing 22–43% nickel, 0.2–1.8% chromium, 1.5–5% iron with the balance being aluminum and incidental impurities. The process is run in aqueous sodium hydroxide and ethanol at 93° C. and a hydrogen pressure of 1160–1305 psi. The yield of AMC is 54%.

Klenke and Gilbert, Journal of Organic Chemistry, (2001), 66, 2480–2483 disclose a method for the reduction of nitrites in the presence of Boc-protected amines using combinations of nickel with palladium on carbon. This reference does not disclose the use of these catalyst combinations to reduce 2-iminonitriles to their corresponding diamines, nor does it disclose the use of a palladium-doped Raney-type nickel for such a conversion.

AMC is a valuable molecule that is useful in the formulation of epoxy-curing agents for polyurethane cross-linkers, for polyamide modifiers, for metal chelating agents and a host of other uses. AMC has been produced from CPI by various catalytic hydrogenation methods. Most of these prior art methods require high pressures of hydrogen, high levels of corrosive sodium hydroxide, or results in low AMC purity and/or yield.

It is the object of the present invention to provide a process for the high yield manufacture of AMC which is economical and which uses relatively low pressure of hydrogen, eliminating the use of high levels of aqueous sodium hydroxide. The combination of these improvements to AMC manufacture affords an easier operation and lower overall cost of production.

BRIEF SUMMARY OF THE INVENTION

Disclosed herein is a process for preparing 2-(aminomethyl)-1-cyclopentylamine, said process comprising: (i) preparing an activated catalyst by combining a suitable solvent and a catalyst system in a vessel purged with an inert gas, pressurized with hydrogen to about 50–500 psi at a temperature of about 25° C. to about 50° C., wherein said catalyst system comprises either nickel and palladium, wherein said palladium is supported on carbon, or palladium-doped Raney type nickel; (ii) contacting said activated catalyst with 1-amino-2-cyano-1-cyclopentene, at least an equimolar portion of anhydrous ammonia, and a solution of an aqueous inorganic base selected from the group consisting of sodium hydroxide, lithium hydroxide and potassium hydroxide; (iii) pressurizing the vessel by raising the temperature of the vessel to a temperature of about 50° C. to about 150° C. and a pressure of hydrogen of about from 500 psi to about 1500 psi and maintaining said temperature and pressure for a time sufficient to obtain crude 2-(aminomethyl)-1-cyclopentylamine; (iv) separating crude 2-(aminomethyl)-1-cyclopentylamine product; and (v) optionally, purifying crude 2-(aminomethyl)-1-cyclopentylamine to obtain purer 2-(aminomethyl)-1-cyclopentylamine.

DETAILED DESCRIPTION OF THE INVENTION

Described herein is a process for low pressure hydrogenation of CPI to AMC in the presence of (i) a dual, or combined, catalyst system comprising the combination of nickel with palladium, wherein the palladium is supported on carbon, or (ii) palladium-doped Raney-type nickel. The process is carried out at pressures of about 500 to about 1500 psi $H_2$, temperatures of about 50° C. to about 150° C., with added ammonia and inorganic aqueous base for about 1 to about 12 hours.

The catalysts used herein are slurry-type particles and must be pre-activated in a suitable solvent system at a pressure of about 50 to about 500 psi $H_2$, from about 25 to about 50° C. for about 1 to 4 hours prior to charging the CPI to the process. The starting 2-iminonitrile, which is 1-amino-2-cyano-1-cyclopentene (CPI), is produced by the base catalyzed cyclization of adiponitrile. This method is disclosed in Thompson, Q. E.; J. Am. Chem. Soc., (1958), 80, 5483–5487. Treatment of adiponitrile with a sterically hindered base, such as sodium t-butoxide (1:1 mole equivalent) in a non-polar aromatic solvent such as toluene, produces CPI in approximately 75% yield and greater than about 97% purity.

Suitable catalysts for the low pressure hydrogenation of CPI include the combination of a nickel-containing catalyst, preferably unsupported metallic nickel or skeletal nickel (for example, Degussa Ni B113W, Raney Ni 2800) with about 5 to about 10 wt. % of palladium supported on carbon (for example, Heraeus K0236 10% palladium on carbon) or a single catalyst system of palladium-doped Raney Ni 2000. The Pd-doped Raney Ni catalyst is preferred.

When the catalyst system of nickel in combination with palladium on carbon is used the loading of palladium-on-carbon catalyst is about 5–20 wt. % relative to the nickel catalyst, which is equivalent to about 0.25–2 wt. % Pd relative to Ni. In the single catalyst system, which is palladium-doped Raney nickel, the level of palladium doping is about 0.25–1.0 wt. % relative to the nickel content, with about 0.5 wt. % being preferred. Slurry catalysts may be in the form of powder, granules, or other relatively fine particles while fixed-bed catalysts may be used as larger granules, extrudates, tablets, spheres, etc. Total catalyst loading relative to CPI is about 1 g catalyst/10 g CPI, although higher loading may be required for increased rate of conversion. For both catalyst systems, the catalyst is activated prior to use by combining it with water, an aprotic polar organic solvent, a combination of aprotic polar organic solvents, or a combination of aprotic polar organic solvent and water, preferably a solvent blend of dioxane/deionized water (about 3:1 v/v) in the reaction vessel, such as an autoclave, raising the temperature to approximately 25° C.

to about 50° C., purging with 2 volumes of $N_2$, then adding hydrogen to a pressure of about 50 psi to about 500 psi. These conditions are held for about 1–4 hours to activate the catalyst system.

After activation of the catalyst system the low-pressure hydrogenation is carried out in a reaction vessel the presence of hydrogen, typically between about 500 psi to about 1500 psi. Nitrogen or argon is initially used to remove air from the reaction vessel and can be added during the reaction to minimize the effects of trace oxygen on the nickel catalyst. The catalyst is contacted with CPI, at least an equimolar portion of anhydrous ammonia (about a 5/1 mole ratio $NH_3$/CPI is preferred), and a solution of an aqueous inorganic base. Suitable bases include hydroxides of sodium, potassium and lithium.

The reaction vessel where the hydrogenation is carried out is pressurized by raising the temperature of the vessel to a temperature of about 50° C. to about 150° C. and a hydrogen pressure of about 500 psi to about 1500 psi. The temperature and hydrogen pressure is maintained throughout the reaction to maintain catalyst life and to increase conversion and selectivity to AMC. Temperatures of about 50° C. to about 150° C. are preferred for the conversion of CPI to AMC during hydrogenation. It has been observed that higher temperatures of about 150° C. to about 200° C. result in unacceptably higher concentrations of secondary and tertiary amines.

The process of the present invention is carried out in a suitable solvent. Suitable solvents include water, an aprotic polar organic solvent, a combination of aprotic polar organic solvents, or a combination of aprotic polar organic solvent and water. Examples of these include, but are not limited to dioxane, diethyl ether, tetrahydrofuran, water and combinations thereof. A solution comprising dioxane/water combination from about 1:1 v/v dioxane/water to about 5:1 v/v dioxane/water being preferred, with about 3:1 v/v dioxane/water being most preferred.

The process is typically run in a stirred batch mode (slurry catalyst), where the catalyst is activated in the above procedure, after which the CPI, 50% aqueous inorganic base (approximately 2 wt. % of the solution relative to CPI) is charged to the autoclave. The aqueous inorganic base may also be added as the inorganic base with a separate addition of water. When the process is carried out in batch mode, after catalyst activation of step (I), but before contacting the activated catalyst with the CPI, anhydrous ammonia, and aqueous inorganic base, the temperature and pressure are brought to ambient conditions.

The CPI that is used for the process of the present invention may be produced by contacting adiponitrile with a molar equivalent amount of a sterically hindered base in a non-polar, aromatic solvent. That CPI may be isolated and dissolved in dioxane/water solution.

Purification of AMC may be carried out, and is accomplished by separation of the reaction mixture from the catalyst by vacuum filtration under an inert gas such as $N_2$ or argon, followed by vacuum distillation. AMC is a useful molecule, for example, in the formulation of epoxy curing agents, for polyurethane cross-linkers, for polyamide modifiers, for metal chelating agents, etc.

EXAMPLES

Example 1

Hydrogenation of 1-amino-2-cyano-1-cyclopentene (CPI) to 2-aminomethyl-cyclopentylamine (AMC) Using a Mixture of Nickel and Palladium/Carbon 30 grams of wet Degussa nickel catalyst (B113W), 5 grams of Heraeus K0236 10% Pd/C catalyst, 480 mL of 1,4-dioxane, and 160 mL deionized water were charged to a 1000 cc autoclave. The mixture was $N_2$ purged in the autoclave with 2 volumes of nitrogen. The mixture was then activated with hydrogen at 300 psi, 35° C., for 3 hours. The mixture was cooled to room temperature, vented, purged with 2 volumes of nitrogen. 50 grams CPI, 1 gram of 50% aqueous NaOH and 75 grams of anhydrous ammonia were added. The reaction was agitated for 12 hours at 75° C. and 1500 psi of hydrogen, with re-pressuring of hydrogen during the reaction to maintain the pressure at 1500 psi +/–100 psi. At the end of 12 hr the reaction was cooled, vented and rinsed out with deionized water. The reaction mixture was filtered under an atmosphere of $N_2$ through a coarse sintered glass filter funnel, and concentrated in vacuo to a clear, viscous, yellow oil. The oil was distilled using a Vigreaux column with fraction cutter, to collect product at 48° C. and 4 mm Hg pressure. Purity of the product by gas chromatography >99%. Product yield was 65%.

Example 2

Hydrogenation of CPI to AMC Using a Palladium-Promoted Raney 2000 Nickel

The same pre-treatment of catalyst was done as in Example 1, with the exception that the catalyst was 0.5 wt. % palladium-promoted Raney Ni 2000. One gram of catalyst plus 10 grams of starting CPI was heated and stirred 6 hr at 150° C. with 1500 psi $H_2$ (with re-pressure) and excess $NH_3$. Gas chromatography showed 100% conversion and >95% selectivity to AMC.

Comparative Example 1

Hydrogenation CPI to AMC with 5% Pd/C to Show the Effect of Not Adding Ni 50 mL of dioxane, 15 mL of Dl water and 2 grams of 5% Heraeus K0203 Pd/C were charged to a 100 cc autoclave. The mixture was pressurized to 300 psi with $H_2$ for 3 hours at 35° C. The mixture was cooled to room temperature, vented, and then 5 g of CPI were added followed by 4 g of anhydrous ammonia. The vessel was pressurized to 1500 psi with $H_2$ at 150° C. (re-pressurizing as necessary) and heated for 6 hr. The mixture was then cooled to room temperature, vented, purged with 3 volumes of $N_2$ and analyzed by gas chromatography. The product was 92% unreacted CPI and 0% AMC.

Comparative Example 2

Hydrogenation CPI to AMC with Ni to Show the Effect of Not Adding Pd/C)

50 mL of dioxane, 15 mL of Dl water and 2 grams Degussa-Huls B111W nickel were charged to a 100 cc autoclave. The mixture was pressurized to 300 psi with $H_2$ for 3 hours at 35° C. The mixture was cooled to room temperature, vented, and then 5 g of CPI were added followed by 4 g of anhydrous ammonia. The vessel was pressurized to 1500 psi with $H_2$ at 150° C. (re-pressurizing as necessary) and heated for 6 hr. The mixture was then cooled to room temperature, vented, purged with 3 volumes of $N_2$ and analyzed by gas chromatography. The product contained 95% unreacted CPI and 0% AMC.

Comparative Example 3

Hydrogenation CPI to AMC with 5% Pd/C to Show the Effects of Not Adding Ni, Changing the Solvent Mixture to Methanol, Lowering the Temperature and Pressure Five grams of CPI were charged to a 100 cc autoclave with 25 mL of methanol, 1 g of $NH_3$ and 1 g of Heraeus K0227 5% Pd/C catalyst. The autoclave was purged 3× with N$_2$, then heated to 60° C. and with 300 psi H$_2$ for 6 hours. The reaction mixture was cooled to room temperature, purged 3× with N$_2$ and suctioned out of the autoclave. Gas chromatography of the product showed 99% unreacted CPI.

Comparative Example 4

Hydrogenation of CPI to AMC with Ni to Show the Effect of Not Adding Pd, Changing the Solvent Mixture to Methanol, Lowering the Pressure The same procedure and equipment were used as in comparative example 3 with 5 g CPI, 0.2 g of Degussa-Huls B111W nickel slurry, 150° C., 1000 psi H$_2$, and 1 g of NH$_3$ in 50 mL of methanol for 1 hour. Gas chromatography shows predominately unreacted CPI with no evidence of AMC.

What is claimed is:

1. A process for preparing 2-(aminomethyl)-1-cyclopentylamine, said process comprising:
   (i) preparing an activated catalyst by combining a suitable solvent and a catalyst system in a vessel purged with an inert gas, pressurized with hydrogen to about 50–500 psi at a temperature of about 25° C. to about 50° C., wherein said catalyst system comprises either nickel and palladium, wherein said palladium is supported on carbon, or palladium-doped Raney type nickel
   (ii) contacting said activated catalyst with 1-amino-2-cyano-1-cyclopentene, at least an equimolar portion of anhydrous ammonia, and a solution of an aqueous inorganic base selected from the group consisting of sodium hydroxide, lithium hydroxide and potassium hydroxide;
   (iii) pressurizing the vessel by raising the temperature of the vessel to a temperature of about 50° C. to about 150° C. and a pressure of hydrogen of about from 500 psi to about 1500 psi and maintaining said temperature and pressure for a time sufficient to obtain crude 2-(aminomethyl)-1-cyclopentylamine;
   (iv) separating crude 2-(aminomethyl)-1-cyclopentylamine product; and
   (v) optionally, purifying crude 2-(aminomethyl)-1-cyclopentylamine to obtain purer 2-(aminomethyl)-1-cyclopentylamine.

2. The process of 1 wherein said 1-amino-2-cyano-1-cyclopentene of step (ii) is obtained by contacting adiponitrile with a molar equivalent amount of a sterically hindered based in a non-polar, aromatic solvent to produce 1-amino-2-cyano-1-cyclopentene; and isolating the 1-amino-2-cyano-1-cyclopentene product of step.

3. The process of claim 2 wherein the 1-amino-2-cyano-1-cyclopentene of step (ii) is dissolved in dioxane/water solvent.

4. The process of claim 1 wherein said process is run in a batch mode and wherein said process further comprises, after step (i) and before step (ii) reducing the temperature and pressure to ambient conditions.

5. The process according to claims 1 or 3 wherein the 2-(aminomethyl)-1-cyclopentylamine is purified by distillation.

6. The process of claims 1 or 3 wherein said suitable solvent is water, an aprotic polar organic solvent, a combination of aprotic polar organic solvents, or a combination of aprotic polar organic solvent and water.

7. The process of claim 6 wherein said suitable solvent is a dioxane/water solution.

* * * * *